United States Patent
Chang et al.

(10) Patent No.: US 11,135,165 B2
(45) Date of Patent: Oct. 5, 2021

(54) SUSPENSION COMPRISING ALUMINUM HYDROXIDE AND MAGNESIUM HYDROXIDE AND PREPARATION METHOD THEREFOR

(71) Applicants: Daewoong Pharmaceutical Co., Ltd., Hwaseong-si (KR); Liaoning Daewoong Pharmaceutical Co., Ltd., Benxi (CN)

(72) Inventors: Ye Chang, Benxi (CN); Qing Ri Li, Benxi (CN); Sang Ho Seol, Benxi (CN); Tie Li, Benxi (CN); Chao Tong, Benxi (CN)

(73) Assignees: Daewoong Pharmaceutical Co., Ltd., Hwaseong-si (KR); Liaoning Daewoong Fharmaceutcal Co., Ltd., Benxi (CN)

( * ) Notice: Subject to any disclaimer, the term of this patent is extended or adjusted under 35 U.S.C. 154(b) by 0 days.

(21) Appl. No.: 16/604,167

(22) PCT Filed: Apr. 12, 2018

(86) PCT No.: PCT/KR2018/004305
§ 371 (c)(1),
(2) Date: Oct. 10, 2019

(87) PCT Pub. No.: WO2018/190659
PCT Pub. Date: Oct. 18, 2018

(65) Prior Publication Data
US 2020/0113826 A1    Apr. 16, 2020

(30) Foreign Application Priority Data

Apr. 13, 2017  (CN) .......................... 201710240597.0

(51) Int. Cl.
| | | |
|---|---|---|
| *A61K 9/10* | (2006.01) | |
| *A61K 33/08* | (2006.01) | |
| *A61K 47/34* | (2017.01) | |
| *A61K 47/36* | (2006.01) | |
| *A61K 47/38* | (2006.01) | |

(52) U.S. Cl.
CPC ................ *A61K 9/10* (2013.01); *A61K 33/08* (2013.01); *A61K 47/34* (2013.01); *A61K 47/36* (2013.01); *A61K 47/38* (2013.01)

(58) Field of Classification Search
CPC .......... A61K 9/10; A61K 33/08; A61K 47/34; A61K 47/36; A61K 47/38
See application file for complete search history.

(56) References Cited

U.S. PATENT DOCUMENTS

| | | | |
|---|---|---|---|
| 3,272,704 A | 9/1966 | Beckman | |
| 3,591,680 A * | 7/1971 | Greene | ................ A61K 9/0095 |
| | | | 424/601 |
| 4,443,433 A | 4/1984 | Knecht et al. | |
| 5,272,137 A | 12/1993 | Blase et al. | |
| 5,593,489 A | 1/1997 | Wu | |
| 2003/0232092 A1* | 12/2003 | Hasenmayer | ........ A61K 9/0095 |
| | | | 424/683 |
| 2013/0243888 A1 | 9/2013 | Ford | |

FOREIGN PATENT DOCUMENTS

| | | |
|---|---|---|
| CN | 104173372 | 12/2014 |
| EP | 0990438 | 4/2000 |
| KR | 10-2000-0023335 | 4/2000 |
| KR | 10-2001-0086297 | 9/2001 |
| KR | 10-0726690 | 6/2007 |
| KR | 10-2008-0081071 | 9/2008 |
| WO | WO 00/40254 | 7/2000 |
| WO | WO 2018/190659 | 10/2018 |

OTHER PUBLICATIONS

International Search Report and the Written Opinion dated Jul. 30, 2018 From the International Searching Authority Re. Application No. PCT/KR2018/004305 and Its Translation of Search Report Into English. (8 Pages).
Examination Report Under Sections 12 & 13 of the Patents Act, 1970 and the Patents Rules, 2003 dated Mar. 5, 2020 From the Government of India, Intellectual Property India, Patents, Designs, Trade Marks, Geographical Indications Re. Application No. 201937041255. (6 Pages).
Supplementary European Search Report and the European Search Opinion Dated Aug. 14, 2020 From the European Patent Office Re. Application No. 18783778.6. (5 Pages).

* cited by examiner

*Primary Examiner* — Michael B. Pallay

(57) ABSTRACT

The present invention provides a suspension comprising aluminum hydroxide and magnesium hydroxide and a method of preparing the same. The aqueous suspension composition according to the present invention ensures an excellent sedimentation rate by using a mixed suspending agent with a specific composition, so that insoluble aluminum hydroxide and magnesium hydroxide do not easily settle, do not form a cake, and are easily redispersed. Since the aqueous suspension composition having an excellent sedimentation rate has not only physical stability, but also forms a homogeneous dispersion system, the reproducibility or effectiveness of bioavailability may be ensured. In addition, the aqueous suspension composition according to the present invention provides an excellent texture, and thus patient compliance increases.

11 Claims, No Drawings

SUSPENSION COMPRISING ALUMINUM HYDROXIDE AND MAGNESIUM HYDROXIDE AND PREPARATION METHOD THEREFOR

RELATED APPLICATIONS

This application is a National Phase of PCT Patent Application No. PCT/KR2018/004305 having International filing date of Apr. 12, 2018, which claims the benefit of priority of Chinese Patent Application No. 201710240597.0 filed on Apr. 13, 2017. The contents of the above applications are all incorporated by reference as if fully set forth herein in their entirety.

FIELD AND BACKGROUND OF THE INVENTION

The present invention relates to a suspension comprising aluminum hydroxide and magnesium hydroxide and a method of preparing the same.

A composite formulation of aluminum hydroxide and magnesium hydroxide is widely used worldwide, because it has excellent antacid ability, no interaction between two ingredients, does not interact with food, alcohol and other antacids, and does not cause rebound acid hypersecretion or metabolic alkalosis.

Generally, suspensions are preferred over tablets or powder, because liquid suspensions are more rapidly and effectively dissolved, and have an excellent ability to react with and neutralize stomach acid.

However, to prepare a suspension, it should be considered that solid particles do not easily settle even if the formulation is left untreated, and the settled particles do not form a cake, which is a hard sediment, and are easily redispersed. When the formulation is shaken before use, the particles should be redispersed. In addition, consideration should also be given to a texture, an ease of packing/filling and the prevention of microbial contamination when the formulation is taken by a patient.

In order to stabilize a suspension dispersed in a solution, unless it is prepared and taken immediately, it is necessary to use a large amount of suspending agent. However, if a large amount of suspending agent is used, bioavailability may be generally changed, and therefore, it is desirable to reduce the amount of a suspending agent.

With regard to the selection of a suspending agent that can be used in the preparation of a suspension, Korean Patent No. 10-0726690 (Patent Document 1) shows that a suspending agent tends to undergo thermal gelation in the temperature range used in a pasteurization process, it is already restricted that the choice of an available suspending agent interact with metal ions, and hydroxypropyl methylcellulose (HPMC) is most generally used because it is generally considered that HPMC is most suitable because of miscibility with an antacid (metal ions) and pasteurization at a mild temperature such as 60 to 70° C. It also shows that, when hydroxyethyl cellulose is used as a suspending agent, sterilization can be easily performed at a low temperature without fear of the hardening of the suspending agent.

However, in the prior art documents including Patent Document 1, it has not been reported that the use of a specific combination of suspending agents can improve problems of the sedimentation rate and the texture of a suspension.

SUMMARY OF THE INVENTION

The present invention relates to a suspension comprising aluminum hydroxide and magnesium hydroxide, which can improve the sedimentation rate, texture and viscosity of the suspension, and a method of preparing the same.

Technical Solution

Generally, as a suspending agent used in an aqueous suspension composition comprising aluminum hydroxide and magnesium hydroxide, a cellulose-based suspending agent such as HPMC has been used, and a single suspending agent has been used in most cases.

However, the inventors found that a single suspending agent has problems in, for example, the sedimentation rate and texture of a suspension, and in order to solve these problems, a specific combination of mixed suspending agents was used, and thus the problems in, for example, the sedimentation rate and texture of the suspension are improved.

Specifically, the present invention provides an aqueous suspension composition, which comprises aluminum hydroxide, magnesium hydroxide, a mixed suspending agent and an antifoaming agent, wherein the mixed suspending agent is a mixture of hydroxypropyl methylcellulose, microcrystalline cellulose, sodium carboxymethyl cellulose and carrageenan.

As can be seen from the following examples, compared to aqueous suspension compositions comprising each of hydroxypropyl methylcellulose (Comparative Example 1), carrageenan (Comparative Example 2), microcrystalline cellulose and sodium carboxymethyl cellulose (Comparative Example 3) as a single suspending agent, it was confirmed that an aqueous suspension composition using a mixed suspending agent consisting of hydroxypropyl methylcellulose, microcrystalline cellulose, sodium carboxymethyl cellulose and carrageenan is excellent in terms of sedimentation rate and texture.

The aqueous suspension composition comprising the aluminum hydroxide and the magnesium hydroxide is used to treat or alleviate hypergastric acidity, heartburn, gastric discomfort, gastric distension, indigestion (dyspepsia), nausea, vomiting, stomachaches, sour burps or the like.

In this aqueous suspension composition, the aluminum hydroxide and the magnesium hydroxide are included as antacids.

In an exemplary embodiment of the present invention, the content of each of the aluminum hydroxide and the magnesium hydroxide, with respect to the aqueous suspension composition, may be 3 to 5% (w/v), but the present invention is not limited thereto. For example, the content of each of the aluminum hydroxide and the magnesium hydroxide, with respect to the aqueous suspension composition, may be 3.5 to 4.5% (w/v), for example, 3.9 to 4.1% (w/v). For reference, the content of the aluminum hydroxide, calculated with $Al_2O_3$, may be approximately 1.5 to 2.5% (w/v), which may be expressed as a value corresponding to ½ of the above-mentioned content.

The aqueous suspension composition according to the present invention includes a mixture of hydroxypropyl methylcellulose, microcrystalline cellulose, sodium carboxymethyl cellulose and carrageenan as a mixed suspending agent.

According to an exemplary embodiment of the present invention, the content of hydroxypropyl methylcellulose, with respect to the aqueous suspension composition, may be 0.4 to 0.9% (w/v). For example, the content of hydroxypropyl methylcellulose, with respect to the aqueous suspension composition, may be 0.45 to 0.9% (w/v), 0.5 to 0.85% (w/v), 0.55 to 0.8% (w/v), 0.55 to 0.75% (w/v), or 0.6 to 0.7% (w/v).

According to an exemplary embodiment of the present invention, both of the microcrystalline cellulose and the sodium carboxymethyl cellulose used in the mixed suspending agent may be used in the form of an excipient such as Avicel RC-581, which includes the two components, or each of the microcrystalline cellulose and the sodium carboxymethyl cellulose may be used as an independent ingredient.

According to an exemplary embodiment of the present invention, the content of the mixture of the microcrystalline cellulose and the sodium carboxymethyl cellulose, with respect to the aqueous suspension composition, may be 0.1 to 0.5% (w/v). For example, the content of the mixture of the microcrystalline cellulose and the sodium carboxymethyl cellulose, with respect to the aqueous suspension composition, may be 0.1 to 0.4% (w/v), for example, 0.1 to 0.3% (w/v), 0.1 to 0.25% (w/v), or 0.1 to 0.2% (w/v).

In addition, the content ratio of the microcrystalline cellulose and the sodium carboxylmethyl cellulose may be 7:1 to 9:1. For example, the content ratio of the microcrystalline cellulose and the sodium carboxylmethyl cellulose may be 7.5:1 to 8.5:1.

Meanwhile, the content of the carrageenan, with respect to the aqueous suspension composition, may be 0.1 to 0.3% (w/v). For example, the content of the carrageenan, with respect to the aqueous suspension composition, may be, for example, 0.1 to 0.25% (w/v) or 0.1 to 0.2% (w/v).

The content of the aluminum hydroxide (calculated with $Al_2O_3$) is preferably 0.02 g/mL, and the content of the magnesium hydroxide is preferably 0.04 g/mL.

The aqueous suspension composition according to the present invention may comprise an antifoaming agent ingredient, as well as the above-described ingredients.

In the present invention, as antifoaming agents, simethicone and a silicone resin may be used, but the present invention is not particularly limited thereto.

With respect to the aqueous suspension composition, the content of the simethicone may be 0.01 to 0.05% (w/v), for example, 0.02 to 0.04% (w/v), and the content of the silicone resin may be 0.2 to 0.8% (w/v), for example, 0.3 to 0.6% (w/v), but the present invention is not limited thereto. The simethicone may be included in the suspension in the form of a simethicone emulsion and for example, the content of a simethicone 30% emulsion, with respect to the aqueous suspension composition, may be 0.05 to 0.15%.

The aqueous suspension composition according to the present invention may further comprises other additives that can be included in the suspension composition. For example, one or more of a sweetener, a preservative, a corrigent, a flavoring agent, and a coloring agent may be further included.

Ingredients that can be used as a sweetener, a preservative, a corrigent, a flavoring agent and a coloring agent are not particularly limited, and can be suitable selected by one of ordinary skill in the art.

In an exemplary embodiment of the present invention, a sweetener may be stevioside, a preservative may be chlorohexidine acetate, a corrigent may be sorbitol, and a flavoring agent may be orange flavor essence, but the present invention is not limited thereto.

The aqueous suspension composition according to the present invention provides an excellent sedimentation rate by using a mixed suspending agent with a specific composition, which has been described above.

The aqueous suspension composition according to the present invention has a sedimentation rate of 0.97 to 1, which meets the requirements of Pharmacopoeia. The sedimentation rate in the above range means that a uniform dispersion system can be obtained together with the physical stability of the suspension. In a water-insoluble composite suspension comprising aluminum hydroxide and magnesium hydroxide, a suspension with a homogeneous dispersion system means that the bioavailability of a drug can be reproduced or effective.

The aqueous suspension composition according to the present invention also provides an excellent texture by using a mixed suspending agent with a specific composition ratio.

The composition ratio of the mixed suspending agent according to an exemplary embodiment of the present invention is associated with the texture of the aqueous suspension composition.

Since an oral suspension composition such as the aqueous suspension composition according to the present invention contains powder particles of an insoluble drug, the suspension may have a bad texture, which may cause discomfort in a patient. Therefore, texture may be a very important factor for increasing patient compliance.

As can be seen in the following examples, the composition ratio of the mixed suspending agent according to the exemplary embodiment of the present invention significantly improves the texture of the aqueous suspension composition.

Meanwhile, the present invention provides a method of preparing an aqueous suspension composition according to the present invention, which comprises:

a) preparing a first aqueous solution comprising hydroxypropyl methylcellulose, microcrystalline cellulose and sodium carboxymethyl cellulose, a second aqueous solution comprising an antifoaming agent, and a third aqueous solution comprising carrageenan;

b) mixing the first aqueous solution and the second aqueous solution and adding and stirring aluminum hydroxide and magnesium hydroxide in the mixed solution;

c) homogenizing the solution obtained in step b);

d) adding and stirring the third aqueous solution in the homogenized solution obtained in step c); and e) adding and stirring an additive in the solution obtained in step d), adding purified water and quantifying the resulting solution.

More specifically, the aqueous suspension composition according to the present invention may be prepared by the method to be described below.

1. Preparation of Solution 1.1) Preparation of Solution 1: A corrigent was added to purified water and stirred for 5 to 10 minutes, hydroxypropyl methylcellulose was added thereto and stirred for 5 to 10 minutes, microcrystalline cellulose and sodium carboxymethyl cellulose were added thereto and stirred for 30 to 60 minutes to confirm complete dispersion, and then swollen;

1.2) Preparation of Solution 2: An antifoaming agent was added to purified water and stirred for 10 to 20 minutes, thereby preparing Solution 2; and 1.3) Preparation of Solution 3: Carrageenan was added to purified water and dissolved by being stirred for 20 to 40 minutes at 80 to 100° C., thereby preparing Solution 3.

2. Mixing 2.1) Solution 2 was mixed with Solution 1, and then stirred for 5 to 10 minutes.

2.2) The solution obtained in 2.1) was mixed with aluminum hydroxide and magnesium hydroxide, and then stirred for 10 to 20 minutes.

3. Homogenization

The solution obtained in 2.2) was homogenized as follows.

3.1) First homogenization: a primary pressure was set to 130 to 150 bar, a secondary pressure was set to 26 to 30 bar, the solution was homogenized, and then the inside of a homogenizer was washed with purified water.

3.2) Second homogenization: a primary pressure was set to 140 to 160 bar, a secondary pressure was set to 28 to 32 bar, the solution was homogenized, and then the inside of a homogenizer was washed with purified water.

3.3) Third homogenization: a primary pressure was set to 160 to 180 bar, a secondary pressure was set to 38 to 42 bar, the solution was homogenized, and then the inside of a homogenizer was washed with purified water.

4. Quantification 4.1) Solution 3 was added to the homogenized solution obtained in 3.3), and then stirred for 10 to 20 minutes.

4.2) Chlorhexidine acetate, stevioside and orange flavor were added to the solution obtained in 4.1), and then stirred for 5 to 10 minutes.

4.3) The resulting solution was quantified with purified water, and then stirred for 5 to 15 minutes.

In an exemplary embodiment of the present invention, the preparation method will be described as follows.

1. Preparation of solution 1.1) Preparation of Solution 1: A sorbitol solution was added to purified water, stirred for 5 minutes, HPMC was added thereto and stirred for 5 minutes, microcrystalline cellulose and sodium carboxymethyl cellulose were added thereto and stirred for 40 minutes to confirm complete dispersion, and then swollen;

1.2) Preparation of Solution 2: A simethicone emulsion and a silicone resin were added to purified water, and stirred for 15 minutes, thereby preparing Solution 2;

1.3) Preparation of Solution 3: Carrageenan was added to purified water, and stirred for 30 minutes at 90° C., thereby preparing Solution 3.

2. Mixing 2.1) Solution 2 was mixed with Solution 1, and then stirred for 5 minutes.

2.2) The solution obtained in 2.1) was mixed with aluminum hydroxide and magnesium hydroxide, and then stirred for 15 minutes.

3. Homogenization

The solution obtained in 2.2) was homogenized as follows.

3.1) First homogenization: a primary pressure was set to 140 bar, a secondary pressure was set to 28 bar, the solution was homogenized, and then the inside of a homogenizer was washed with purified water.

3.2) Second homogenization: a primary pressure was set to 150 bar, a secondary pressure was set to 30 bar, the solution was homogenized, and then the inside of a homogenizer was washed with purified water.

3.3) Third homogenization: a primary pressure was set to 170 bar, a secondary pressure was set to 40 bar, the solution was homogenized, and then the inside of a homogenizer was washed with purified water.

4. Quantification 4.1) Solution 3 was added to the homogenized solution obtained in 3.3), and then stirred for 15 minutes.

4.2) A sweetener, a preservative and a flavoring agent were added to the solution obtained in 4.1), and then stirred for 5 minutes.

4.3) The resulting solution was quantified with purified water, and then stirred for 10 minutes.

Advantageous Effects

An aqueous suspension composition according to the present invention ensures an excellent sedimentation rate by using a mixed suspending agent with a specific composition, such that insoluble aluminum hydroxide and magnesium hydroxide do not easily settle, do not form a cake, and are easily redispersed. Since the aqueous suspension composition having an excellent sedimentation rate not only has physical stability, but also forms a homogeneous dispersion system, the reproducibility or effectiveness of bioavailability can be ensured. In addition, the aqueous suspension composition according to the present invention provides an excellent texture, thereby increasing patient compliance.

DESCRIPTION OF SPECIFIC EMBODIMENTS OF THE INVENTION

Hereinafter, the advantages and features of the present invention and the methods of accomplishing the same may be clearly understood with reference to the detailed description of exemplary embodiments. However, the present invention is not limited to the exemplary embodiments disclosed below, and may be embodied in many different forms. These exemplary embodiments are merely provided to complete the disclosure of the present invention and fully convey the scope of the present invention to those of ordinary skill in the art, and the present invention should be defined by only the accompanying claims.

EXAMPLES

Measurement of Viscosity

Viscosity values were obtained using a LV 2(62) spindle at room temperature (20 to 25° C.) with a Brookfield viscometer (BROOKFIELD LVDV-I Prime; serial Number 8570291).

Measurement of Sedimentation Rate

A sample was placed in a 50 mL mass cylinder at room temperature, mixed by being shaken vigorously for 1 minute, and the height of the content, which was called $H_0$, was marked and the final height of the content after standing for 3 hours was set to $H_0$. And then, the sedimentation rate was calculated by Equation 1 below.

$$\text{Sedimentation rate} = H/H_0 \quad \text{Equation 1}$$

Method of Evaluating Texture

The panel consisted of a total of ten male and female adults, and an average was determined by adding up the scores of each panelist based on 10 out of 10 points per sample.

Preparation Example I

Aqueous suspension compositions of Examples and Comparative Examples were prepared according to the above-described preparation method.

Example 1

0.2 g of aluminum hydroxide (calculated with $Al_2O_3$), 0.4 g of magnesium hydroxide, 0.055 g of hydroxypropyl methylcellulose, 0.02 g of microcrystalline cellulose and sodium carboxymethyl cellulose, 0.015 g of carrageenan, 2.5 g of a sorbitol solution (concentration: 0.25 g/ml), 0.008 g of simethicone, 0.04 g of a silicone resin, 0.002 g of stevioside, 0.0015 g of chlorhexidine acetate, 0.5 g of orange flavor essence and the remainder as purified water up to 10 mL were included. As a result of detection, the sedimentation rate of the product was 0.98, the viscosity of the product was relatively small, which was 470 mPa·s, and the texture was smooth.

Example 2

0.2 g of aluminum hydroxide (calculated with $Al_2O_3$), 0.4 g of magnesium hydroxide, 0.065 g of hydroxypropyl methylcellulose, 0.02 g of microcrystalline cellulose and sodium carboxymethyl cellulose, 0.015 g of carrageenan, 2.5 g of a sorbitol solution, 0.008 g of simethicone, 0.04 g of a silicone resin, 0.002 g of stevioside, 0.0015 g of chlorhexidine acetate, 0.5 g of orange flavor essence and the remainder as purified water up to 10 mL were included. As a result of detection, the sedimentation rate of the product was 1.0, the viscosity of the product was relatively small, which was 540 mPa·s, and the texture was smooth.

Example 3

0.2 g of aluminum hydroxide (calculated with $Al_2O_3$), 0.4 g of magnesium hydroxide, 0.055 g of hydroxypropyl methylcellulose, 0.015 g of microcrystalline cellulose and sodium carboxymethyl cellulose, 0.01 g of carrageenan, 2.5 g of a sorbitol solution, 0.008 g of simethicone, 0.04 g of a silicone resin, 0.002 g of stevioside, 0.0015 g of chlorhexidine acetate, 0.5 g of orange flavor essence and the remainder as purified water up to 10 mL were included. As a result of detection, the sedimentation rate of the product was 0.98, the viscosity of the product was relatively small, which was 600 mPa·s, and the texture was smooth.

Example 4

0.2 g of aluminum hydroxide (calculated with $Al_2O_3$), 0.4 g of magnesium hydroxide, 0.085 g of hydroxypropyl methylcellulose, 0.01 g of microcrystalline cellulose and sodium carboxymethyl cellulose, 0.015 g of carrageenan, 2.5 g of a sorbitol solution, 0.008 g of simethicone, 0.04 g of a silicone resin, 0.002 g of stevioside, 0.0015 g of chlorhexidine acetate, 0.5 g of orange flavor essence and the remainder as purified water up to 10 mL were included. As a result of detection, the sedimentation rate of the product was 0.97, the viscosity of the product was relatively small, which was 650 mPa·s, and the texture was smooth.

Example 5

0.2 g of aluminum hydroxide (calculated with $Al_2O_3$), 0.4 g of magnesium hydroxide, 0.045 g of hydroxypropyl methylcellulose, 0.02 g of microcrystalline cellulose and sodium carboxymethyl cellulose, 0.03 g of carrageenan, 2.5 g of a sorbitol solution, 0.008 g of simethicone, 0.04 g of a silicone resin, 0.002 g of stevioside, 0.0015 g of chlorhexidine acetate, 0.5 g of orange flavor essence and the remainder as purified water up to 10 mL were included. As a result of detection, the sedimentation rate of the product was 0.97, the viscosity of the product was relatively small, which was 703 mPa·s, and the texture was smooth.

Comparative Example 1

0.2 g of aluminum hydroxide (calculated with $Al_2O_3$), 0.4 g of magnesium hydroxide, 0.1 g of hydroxypropyl methylcellulose, 2.5 g of a sorbitol solution, 0.008 g of simethicone, 0.04 g of a silicone resin, 0.002 g of stevioside, 0.0015 g of chlorhexidine acetate, 0.5 g of orange flavor essence and the remainder as purified water up to 10 mL were included. As a result of detection, the sedimentation rate of the product was 0.74.

Comparative Example 2

0.2 g of aluminum hydroxide (calculated with $Al_2O_3$), 0.4 g of magnesium hydroxide, 0.6 g of carrageenan, 2.5 g of a sorbitol solution, 0.008 g of simethicone, 0.04 g of a silicone resin, 0.002 g of stevioside, 0.0015 g of chlorhexidine acetate, 0.5 g of orange flavor essence and the remainder as purified water up to 10 mL were included. As a result of detection, the sedimentation rate of the product was 1.0, but the viscosity of the product was relatively large, that is, 1,560 mPa·s, and the texture was not good.

Comparative Example 3

0.2 g of aluminum hydroxide (calculated with $Al_2O_3$), 0.4 g of magnesium hydroxide, 0.03 g of microcrystalline cellulose and sodium carboxymethyl cellulose, 2.5 g of a sorbitol solution, 0.008 g of simethicone, 0.04 g of a silicone resin, 0.002 g of stevioside, 0.0015 g of chlorhexidine acetate, 0.5 g of orange flavor essence and the remainder as purified water up to 10 mL were included. As a result of detection, the sedimentation rate of the product was 0.98, but the viscosity of the product was relatively large, that is, 1,450 mPa·s, and the texture was not good.

As can be seen from Examples and Comparative Examples described above, the present invention satisfies the requirements of Pharmacopoeia by increasing the sedimentation rate of the aluminum magnesium suspension using the mixed suspending agent, and the suspension had a soft texture and thus is more easily taken.

Preparation Example II

Based on the effect of the mixed suspending agents that were confirmed in Examples 1 to 4, Examples 6 to 20 were prepared by varying the composition ratio of the mixed suspending agent with the following composition.

TABLE 1

| | Example 6 | Example 7 | Example 8 | Example 9 | Example 10 | Example 11 | Example 12 | Example 13 |
|---|---|---|---|---|---|---|---|---|
| $Al(OH)_3$ (g) | 39.98 | 39.98 | 39.98 | 39.98 | 39.98 | 39.98 | 39.98 | 39.98 |
| $Mg(OH)_2$ (g) | 40 | 40 | 40 | 40 | 40 | 40 | 40 | 40 g |
| Simethicone Emulsion, 30% (g) | 0.84 | 0.84 | 0.84 | 0.84 | 0.84 | 0.84 | 0.84 | 0.84 |
| H.P.M.C. 2208(4000 cps) (g) | 4.5 | 4.5 | 4.5 | 4.5 | 4.5 | 6.5 | 6.5 | 6.5 |

TABLE 1-continued

|  | Example 6 | Example 7 | Example 8 | Example 9 | Example 10 | Example 11 | Example 12 | Example 13 |
|---|---|---|---|---|---|---|---|---|
| Carrageenan (CST # 7632) (g) | 0.5 | 1 | 1.5 | 2 | 2.5 | 0.5 | 1 | 1.5 |
| Avicel RC-581 (g) | 0.5 | 1 | 2 | 3 | 4 | 0.5 | 1 | 2 |
| D-sorbitol, 70% (g) | 250 | 250 | 250 | 250 | 250 | 250 | 250 | 250 |
| Stevioside (g) | 0.2 | 0.2 | 0.2 | 0.2 | 0.2 | 0.2 | 0.2 | 0.2 |
| Silicone resin (30%) (g) | 4 | 4 | 4 | 4 | 4 | 4 | 4 | 4 |
| Chlorhexidine acetate (g) | 0.15 | 0.15 | 0.15 | 0.15 | 0.15 | 0.15 | 0.15 | 0.15 |
| Orange flavor (g) | 5 | 5 | 5 | 5 | 5 | 5 | 5 | 5 |
| Total volume (with distilled water, q.s.) | 1L | 1L | 1L | 1L | 1L | 1L | 1L | 1L |

TABLE 2

|  | Example 14 | Example 15 | Example 16 | Example 17 | Example 18 | Example 19 | Example 20 |
|---|---|---|---|---|---|---|---|
| Al(OH)$_3$ (g) | 39.98 | 39.98 | 39.98 | 39.98 | 39.98 | 39.98 | 39.98 |
| Mg(OH)$_2$ (g) | 40 | 40 | 40 | 40 | 40 | 40 | 40 |
| Simethicone emulsion 30% (g) | 0.84 | 0.84 | 0.84 | 0.84 | 0.84 | 0.84 | 0.84 |
| H.P.M.C. 2208(4000 cps) (g) | 6.5 | 6.5 | 8.5 | 8.5 | 8.5 | 8.5 | 8.5 |
| Carrageenan (CST # 7632) (g) | 2 | 2.5 | 0.5 | 1 | 1.5 | 2 | 2.5 |
| Avicel RC-581 (g) | 3 | 4 | 0.5 | 1 | 2 | 3 | 4 |
| D-sorbitol 70% (g) | 250 | 250 | 250 | 250 | 250 | 250 | 250 |
| Stevioside (g) | 0.2 | 0.2 | 0.2 | 0.2 | 0.2 | 0.2 | 0.2 |
| Silicone resin (30%) (g) | 4 | 4 | 4 | 4 | 4 | 4 | 4 |
| Chlorhexidine acetate (g) | 0.15 | 0.15 | 0.15 | 0.15 | 0.15 | 0.15 | 0.15 |
| Orange flavor (g) | 5 | 5 | 5 | 5 | 5 | 5 | 5 |
| Total volume (with distilled water, q.s.) | 1L | 1L | 1L | 1L | 1L | 1L | 1L |

The texture and sedimentation rate of the aqueous suspension composition of each of Examples 6 to 20 were evaluated.

TABLE 3

| Example | Texture (1~10 points) | Sedimentation rate |
|---|---|---|
| Example 6 | 1 | 1 |
| Example 7 | 3 | 0.99 |
| Example 8 | 8 | 1 |
| Example 9 | 9 | 1 |
| Example 10 | 7 | 0.99 |
| Example 11 | 2 | 0.99 |
| Example 12 | 8 | 1 |
| Example 13 | 10 | 1 |
| Example 14 | 9 | 0.99 |
| Example 15 | 7 | 0.99 |
| Example 16 | 8 | 1 |
| Example 17 | 8 | 1 |
| Example 18 | 7 | 0.99 |
| Example 19 | 7 | 1 |
| Example 20 | 6 | 1 |

As can be seen from Table 3, all of the aqueous suspension compositions of Examples 6 to 20 exhibited a sedimentation rate of 0.99 to 1, indicating that they exhibited excellent sedimentation rates regardless of the composition ratio of the components constituting the mixed suspending agent.

Due to such an excellent sedimentation rate, insoluble aluminum hydroxide and magnesium hydroxide do not easily settle, do not form a cake, and are easily redispersed. The aqueous suspension composition with an excellent sedimentation rate has not only physical stability, but also forms a homogeneous dispersion system, and thus the reproducibility or effectiveness of bioavailability may be ensured.

In addition, for testers orally taking the aqueous suspension compositions of Examples 6 to 20, the higher the texture, the higher the score in the range of 1 to 10, and as a result, when a mixed suspending agent with a specific composition ratio was used, it was confirmed that an excellent texture was provided to patients, confirming that patient compliance can increase.

What is claimed is:

1. An aqueous suspension composition, comprising:
   aluminum hydroxide, magnesium hydroxide, a mixed suspending agent and an antifoaming agent;
   wherein the mixed suspending agent is a mixture of hydroxypropyl methylcellulose, microcrystalline cellulose, sodium carboxymethyl cellulose and carrageenan;
   and wherein the antifoaming agent includes simethicone and a silicone resin.

2. The aqueous suspension composition of claim 1, wherein the contents of the aluminum hydroxide and the magnesium hydroxide are 3 to 5% (w/v) with respect to the aqueous suspension composition, respectively.

3. The aqueous suspension composition of claim 1, wherein the content of the hydroxypropyl methylcellulose is 0.4 to 0.9% (w/v) with respect to the aqueous suspension composition.

4. The aqueous suspension composition of claim 1, wherein the content of a mixture of microcrystalline cellulose and sodium carboxymethyl cellulose is 0.1 to 0.5% (w/v) with respect to the aqueous suspension composition.

5. The aqueous suspension composition of claim 1, wherein the content ratio of the microcrystalline cellulose and the sodium carboxylmethyl cellulose is 7:1 to 9:1.

6. The aqueous suspension composition of claim 1, wherein the content of the carrageenan is 0.1 to 0.3% (w/v) with respect to the aqueous suspension composition.

7. The aqueous suspension composition of claim 1, wherein, with respect to the aqueous suspension composition,
- the content of each of the aluminum hydroxide and the magnesium hydroxide is 3 to 5% (w/v),
- the content of the hydroxypropyl methylcellulose is 0.4 to 0.9% (w/v),
- the content of a mixture of the microcrystalline cellulose and the sodium carboxymethyl cellulose is 0.1 to 0.5% (w/v), and
- the content of carrageenan is 0.1 to 0.3% (w/v).

8. The aqueous suspension composition of claim 1, wherein, with respect to the aqueous suspension composition,
- the content of each of the aluminum hydroxide and the magnesium hydroxide is 3.5 to 4.5% (w/v),
- the content of the hydroxypropyl methylcellulose is 0.45 to 0.85% (w/v),
- the content of a mixture of the microcrystalline cellulose and the sodium carboxymethyl cellulose is 0.1 to 0.4% (w/v), and
- the content of carrageenan is 0.1 to 0.25% (w/v).

9. The aqueous suspension composition of claim 1, wherein, with respect to the aqueous suspension composition, the content of the simethicone is 0.01 to 0.05% (w/v), and the content of the silicone resin is 0.2 to 0.8% (w/v).

10. The aqueous suspension composition of claim 1, further comprising one or more selected from a sweetener, a preservative, a corrigent and a coloring agent.

11. A method of preparing the aqueous suspension composition of claim 1, comprising:
- a) preparing a first aqueous solution comprising hydroxypropyl methylcellulose, microcrystalline cellulose and sodium carboxymethyl cellulose, a second aqueous solution comprising an antifoaming agent, and a third aqueous solution including carrageenan;
- b) mixing the first aqueous solution and the second aqueous solution while stirring, and adding and stirring aluminum hydroxide and magnesium hydroxide in the stirred mixed solution;
- c) homogenizing the solution obtained in step b); and
- d) adding and stirring the third aqueous solution in the homogenized solution obtained in step c); and
- e) adding and stirring an additive in the solution obtained in step d), adding purified water and quantifying the resulting solution.

* * * * *

UNITED STATES PATENT AND TRADEMARK OFFICE
CERTIFICATE OF CORRECTION

PATENT NO. : 11,135,165 B2
APPLICATION NO. : 16/604167
DATED : October 5, 2021
INVENTOR(S) : Chang et al.

It is certified that error appears in the above-identified patent and that said Letters Patent is hereby corrected as shown below:

On the Title Page

Item (73) Assignees, Line 3, "Fharmaceutcal" should be changed to -- Pharmaceutical --

Signed and Sealed this
Fourteenth Day of June, 2022

Katherine Kelly Vidal
*Director of the United States Patent and Trademark Office*